(12) United States Patent
Mabuchi et al.

(10) Patent No.: US 11,007,490 B2
(45) Date of Patent: May 18, 2021

(54) CELLULOSE ACETATE-BASED HOLLOW FIBER MEMBRANE

(71) Applicant: TOYOBO CO., LTD., Osaka (JP)

(72) Inventors: Kimihiro Mabuchi, Osaka (JP); Haruhiko Kohyama, Osaka (JP); Yoshinori Takii, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 16/344,984

(22) PCT Filed: Oct. 31, 2017

(86) PCT No.: PCT/JP2017/039248
§ 371 (c)(1),
(2) Date: Apr. 25, 2019

(87) PCT Pub. No.: WO2018/079808
PCT Pub. Date: May 3, 2018

(65) Prior Publication Data
US 2019/0270051 A1 Sep. 5, 2019

(30) Foreign Application Priority Data
Oct. 31, 2016 (JP) .............................. JP2016-212835

(51) Int. Cl.
*B01D 63/02* (2006.01)
*B01D 69/00* (2006.01)
(Continued)

(52) U.S. Cl.
CPC ............. *B01D 69/081* (2013.01); *A61M 1/34* (2013.01); *A61M 1/3413* (2013.01);
(Continued)

(58) Field of Classification Search
CPC .. B01D 69/02; B01D 71/16; B01D 2325/022; B01D 2325/06
See application file for complete search history.

(56) References Cited

U.S. PATENT DOCUMENTS 5,643,452 A 7/1997 Althin et al.
5,736,046 A 4/1998 Althin et al.
(Continued)

FOREIGN PATENT DOCUMENTS

CN 1049108 A 2/1991
CN 101472671 A 7/2009
(Continued)

OTHER PUBLICATIONS

Tajima, Takatsugu et al—JP 2011-212638 A Machine Translation—Oct. 27, 2011 (Year: 2011).*
(Continued)

*Primary Examiner* — Bradley R Spies
(74) *Attorney, Agent, or Firm* — Westerman, Hattori, Daniels & Adrian, LLP

(57) ABSTRACT

The present invention provides a hollow fiber membrane including a cellulose acetate-based polymer, in which when an inner surface of the hollow fiber membrane is observed under an atomic force microscope, a plurality of groove-like recesses oriented in a lengthwise direction of the hollow fiber membrane are observed, an average length of the recesses is greater than or equal to 200 nm and less than or equal to 500 nm, an average width of the recesses is greater than or equal to 15 nm and less than or equal to 50 nm, and an aspect ratio defined as a ratio of the average length to the average width of each of the recesses is greater than or equal to 6 and less than or equal to 22.

4 Claims, 3 Drawing Sheets

(51) Int. Cl.
  *B01D 69/02* (2006.01)
  *B01D 69/08* (2006.01)
  *B01D 71/16* (2006.01)
  *A61M 1/34* (2006.01)
  *B01D 61/24* (2006.01)
  *D01F 2/28* (2006.01)

(52) U.S. Cl.
  CPC ........... *B01D 61/243* (2013.01); *B01D 63/02* (2013.01); *B01D 69/00* (2013.01); *B01D 69/02* (2013.01); *B01D 69/08* (2013.01); *B01D 71/16* (2013.01); *D01F 2/28* (2013.01); *B01D 2325/022* (2013.01); *B01D 2325/04* (2013.01)

(56) References Cited

U.S. PATENT DOCUMENTS

| | | | |
|---|---|---|---|
| 6,372,136 | B1 | 4/2002 | Nakatsuka |
| 2009/0178969 | A1 | 7/2009 | Hanakawa et al. |
| 2011/0114559 | A1 | 5/2011 | Fislage et al. |
| 2018/0065093 | A1 | 3/2018 | Takada et al. |

FOREIGN PATENT DOCUMENTS

| | | |
|---|---|---|
| CN | 101703893 A | 5/2010 |
| CN | 101883624 A | 11/2010 |
| CN | 102448508 A | 5/2012 |
| DE | 69320000 T2 | 4/1999 |
| EP | 1 029 584 A1 | 8/2000 |
| EP | 3 278 867 A1 | 2/2018 |
| JP | 6-55047 A | 3/1994 |
| JP | 2009-95515 A | 5/2009 |
| JP | 2011-78920 A | 4/2011 |
| JP | 2011-212638 A | 10/2011 |
| WO | 90/05006 A1 | 5/1990 |
| WO | 2010/147763 A2 | 12/2010 |
| WO | 2016/159333 A1 | 10/2016 |

OTHER PUBLICATIONS

International Search Report dated Jan. 23, 2018, issued in counterpart International Application No. PCT/JP2017/039248 (1 page).
Kawanishi, H. et al., "Method of Evaluating Dialyzer Performance, 2012", Journal of Japanese Society of Dialysis Therapy 45(5), pp. 435-445, 2012; with partial English translation.
Extended Search Report dated May 27, 2020, issued in counterpart EP Application No. 17865663.3 (7 pages).
Office Action dated Jul. 15, 2020, issued in U.S. Appl. No. 16/344,153 (7 pages).
Office Action dated Dec. 2, 2020, issued in counterpart in Application No. 201917021292, with English Translation. (5 pages).
Office Action dated Jan. 22, 2021, issued in CN Application No. 201780067442.X (counterpart to U.S. Appl. No. 16/344,153; with English Translation. (14 pages).
Office Action dated Mar. 1, 2021, issued in counterpart CN Application No. 201780067440.0, with English Translation. (16 pages).
Pang, Xinlu (Editor), "Modern Nephrology Theory and Application", Published by Hebei Science & Technology Press, Shijiazuang, Jun. 30, 2013, p. 433, with English Translation.; Cited in CN Office Action dated Mar. 1, 2021. (5 pages).
Notice of Allowance dated Feb. 24, 2021, issued in U.S. Appl. No. 16/344,153 (2 pages).

* cited by examiner

CIRCUMFERENTIAL DIRECTION (2 μm)

← LENGTHWISE DIRECTION (2 μm) →

← INNER SURFACE OF HOLLOW FIBER MEMBRANE

← CIRCUMFERENTIAL DIRECTION (2 μm) →

CIRCUMFERENTIAL DIRECTION (2 μm)

← LENGTHWISE DIRECTION (2 μm) →

← INNER SURFACE OF HOLLOW FIBER MEMBRANE

← CIRCUMFERENTIAL DIRECTION (2 μm) →

CELLULOSE ACETATE-BASED HOLLOW FIBER MEMBRANE

TECHNICAL FIELD

The present invention relates to a hollow fiber membrane made of a cellulose acetate-based polymer. The present invention more specifically relates to a hollow fiber membrane containing a cellulose acetate-based polymer and having an asymmetric structure suitable for a blood purification application, in particular, hemodiafiltration.

BACKGROUND ART

Blood purification includes methods such as hemodialysis, hemofiltration, and hemodiafiltration. The hemodialysis is a method for bringing blood into contact with a dialysis fluid with a semipermeable membrane interposed therebetween to remove a waste product accumulated in a body by means of a diffusion phenomenon. Purified blood is returned to the body again. Normally, the treatment is conducted three times per week, and it takes about four hours per treatment. On the other hand, the hemofiltration is a method for ultra-filtering a large amount of blood to remove a waste product as well as a body fluid. Since a large amount of body fluid is removed, a supplemental fluid (12 to 20 L/time) is required to be supplied. It is said that, although the hemofiltration is superior to the hemodialysis in removal of a medium to high-molecular-weight waste product, the hemofiltration is inferior to the hemodialysis in removal of a low-molecular-weight waste product. Under such circumstances, in recent years, the hemodiafiltration attracts attention since, by combining the hemodialysis with the hemofiltration, the hemodiafiltration enables a wide range of waste products ranging from the low-molecular-weight waste products to the high-molecular-weight waste products to be removed efficiently, and the present applicant has filed related applications (PTL 1 and 2). These patent literatures disclose a hollow fiber membrane applicable to hemodiafiltration and the like. In this hollow fiber membrane, by improving uniformity and smoothness of a membrane surface, adsorption and clogging of blood protein and the like can be restricted even at the time of large-quantity filtration.

CITATION LIST

Patent Literatures

PTL 1: Japanese Patent Laying-Open No. 2009-95515
PTL 2: Japanese Patent Laying-Open No. 2011-78920

Non Patent Literature

NPL 1: Journal of Japanese Society for Dialysis Therapy, 45 (5) 435 to 445 (2012)

SUMMARY OF INVENTION

Technical Problem

The hemodiafiltration therapy includes predilution hemodiafiltration therapy for infusing the fluid into the blood before the blood enters a dialyzer and postdilution hemodiafiltration therapy for infusing the fluid into the blood before the blood exits from the dialyzer. In the predilution hemodiafiltration therapy, since the blood is diluted before entering the dialyzer, the concentration of substances to be removed in the blood is lowered. Although the removing efficiency is lowered due to the diffusion, the predilution hemodiafiltration therapy is advantageous in that protein clogging to the dialyzer is hard to occur, and in that temporal performance degradation is hard to occur. On the other hand, in the postdilution hemodiafiltration therapy, since the hemoconcentration in the dialyzer is significant, problems occur such as an increase in albumin leakage as compared to the predilution hemodiafiltration therapy, and a frequent occurrence of protein clogging to the dialyzer. In general, in the postdilution hemodiafiltration therapy, the required amount of the replacement fluid is about ⅓ of that in the predilution hemodiafiltration therapy to exert an equivalent effect to that in the predilution hemodiafiltration therapy. Thus, further improvement of a hollow fiber membrane is required for adsorption of a smaller amount of protein and restriction of clogging to apply the hollow fiber membrane to the postdilution hemodiafiltration therapy.

An object of the present invention is to provide a hollow fiber membrane that can achieve stable performance suitable for postdilution hemodiafiltration therapy by optimizing a structure of a dense layer on an inner surface of the hollow fiber membrane and to restrict temporal adsorption and clogging of protein.

Solution to Problem

The present invention has the following configuration.
(1) A hollow fiber membrane comprising a cellulose acetate-based polymer, wherein when an inner surface of the hollow fiber membrane is observed under an atomic force microscope, a plurality of groove-like recesses oriented in a lengthwise direction of the hollow fiber membrane are observed, an average length of the recesses is greater than or equal to 200 nm and less than or equal to 500 nm, an average width of the recesses is greater than or equal to 15 nm and less than or equal to 50 nm, and an aspect ratio defined as a ratio of the average length to the average width of each of the recesses is greater than or equal to 6 and less than or equal to 22.
(2) The hollow fiber membrane according to (1), wherein the hollow fiber membrane includes a dense layer on the inner surface side, and a part other than the dense layer has an enlarged pore.
(3) The hollow fiber membrane according to (1) or (2), wherein an inside diameter of the hollow fiber membrane is greater than or equal to 150 μm and less than or equal to 280 μm, and a membrane thickness of the hollow fiber membrane is greater than or equal to 18 μm and less than or equal to 30 μm.
(4) The hollow fiber membrane according to any one of (1) to (3), wherein the cellulose acetate-based polymer is cellulose triacetate.
(5) A hollow fiber membrane module comprising the hollow fiber membrane according to any one of (1) to (4).

Advantageous Effects of Invention

By optimizing a structure of a dense layer on an inner surface of a hollow fiber membrane, it is possible to provide a hollow fiber membrane that can restrict adsorption and clogging of protein and the like even in a case of increases in blood flow rate and/or filtration rate and that is applicable not only to predilution hemodiafiltration therapy but also to postdilution hemodiafiltration therapy.

DESCRIPTION OF EMBODIMENTS

A hollow fiber membrane according to the present invention is in a category of an ultrafiltration membrane. Specifically, an average pore diameter of fine pores of the membrane is approximately several nm to several tens of nm. The membrane has as large fine pores as to prevent a high-molecular-weight substance having a several thousand to several hundred thousand molecular weight and a colloidal substance from being permeated therethrough and to allow a medium-molecular-weight substance having a molecular weight less than or equal to that of the high-molecular-weight substance and ions permeated therethrough.

Conventionally, for blood compatibility and performance improvement, development has been advanced toward enhancement of smoothness of an inner surface of the hollow fiber membrane in order to restrict adsorption and clogging of a blood cell component and plasma protein to the surface of the membrane. However, the conventional development intention has a limitation in responding to increases in blood flow rate and filtration rate. The present inventors have finally arrived at the present invention upon discovering that, by providing a hollow fiber membrane, in which when an inner surface thereof is observed under an atomic force microscope (AFM), a plurality of groove-like recesses oriented in a lengthwise direction of the hollow fiber membrane are observed, an average length of the recesses is greater than or equal to 200 am and less than or equal to 500 nm, an average width of the recesses is greater than or equal to 15 nm and less than or equal to 50 nm, and an aspect ratio (length/width) defined as a ratio of the length to the width of each of the recesses is greater than or equal to 6 and less than or equal to 22, adsorption and clogging of a blood cell component, protein, and the like to the surface of the membrane can further be reduced.

In the present invention, as a material for the hollow fiber membrane, a cellulose acetate-based polymer is preferably used. As the cellulose acetate-based polymer, cellulose diacetate and cellulose triacetate, having some hydroxyl groups capped, are preferable from the viewpoint of restriction of complement activation and blood compatibility such as low blood coagulation. In a case where a hollow fiber membrane mainly including a cellulose-based polymer is used for blood purification, white blood cells may transiently decrease, and this is problematic in terms of blood compatibility. However, using the cellulose acetate-based polymer, having some of the hydroxyl groups of the cellulose substituted with acetyl groups, is advantageous in improvement in blood compatibility. Specifically, relatively-low-viscosity cellulose triacetate having a degree of acetylation of 53 to 62 and a 6% viscosity of more than 140 mPa·s and less than 200 mPa·s is preferable.

Figure 1:
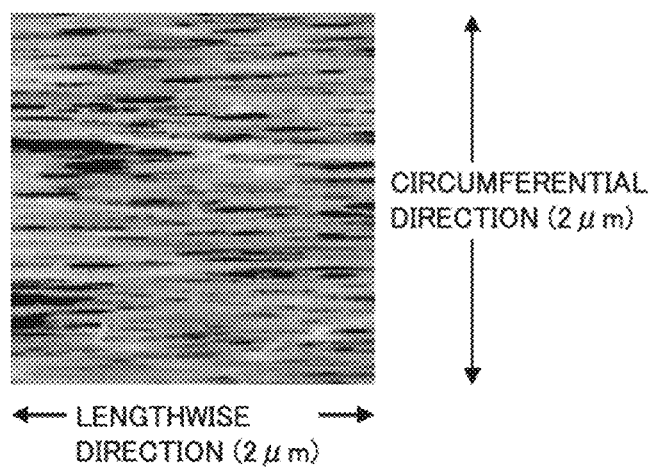
FIG. 1 illustrates a surface shape image when an inner surface of a hollow fiber membrane according to the present invention is observed under an atomic force microscope.

In the present invention, when the inner surface of the hollow fiber membrane is observed using an atomic force microscope under below-mentioned conditions, the surface preferably includes a plurality of groove-like recesses oriented in a lengthwise direction of the hollow fiber membrane (FIG. 1). More specifically, in an about 2 μm-square observation range, the surface preferably includes ten or more groove-like recesses oriented in the lengthwise direction of the hollow fiber membrane. Although the detailed reason is unknown, not only the adsorption of protein and the like is decreased but also the transient decrease of white blood cells tends to be restricted. The reason for this may be that, when the distance between the recesses is within a predetermined range, a blood rectifying effect is enhanced. For this reason, twenty or more recesses are preferably observed on the inner surface.

In the present invention, an average length (long diameter) of the recesses is preferably greater than or equal to 200 nm and less than or equal to 500 nm. In a case where the length of the recess is too short, a blood cell component easily accumulates in the recess. The reason for this may be that the blood rectifying effect is lowered. Thus, in an early stage of treatment, variation of white blood cells (a transient decrease of white blood cells), as an index of biocompatibility, tends to occur significantly. Also, in a case where the length of the recess is too long, this may cause a defect in the membrane surface structure such as breakage of the recess, and biocompatibility may be lowered. Here, the average length (long diameter) is an average value of five values including a highest value and a lowest value as described below.

In the present invention, an average width (short diameter) of the recesses is preferably greater than or equal to 15 nm and less than or equal to 50 nm. In a case where the width of the recess is too short, a sufficient blood rectifying effect cannot be obtained. Thus, in an early stage of treatment, variation of white blood cells (a transient decrease of white blood cells), as an index of biocompatibility, tends to occur significantly. In a case where the width of the recess is too long, a blood cell component easily accumulates in the recess, and temporal performance degradation such as significant variation of white blood cells tends to occur. Here, the average width (short diameter) is an average value of five values including a highest value and a lowest value as described below.

In the present invention, an aspect ratio (average length/average width) defined as a ratio of the average length to the average width of the recesses is preferably greater than or equal to 6 and less than or equal to 22. In a case where the aspect ratio is too low, the recess is in a shape of having a long width for the length. Thus, the blood flow rectifying effect is hard to be obtained, and a blood cell component easily accumulates in the recess. Conversely, a too high aspect ratio probably causes no problem. Nevertheless, an upper limit thereof is likely to be approximately 22.

Figure 2:
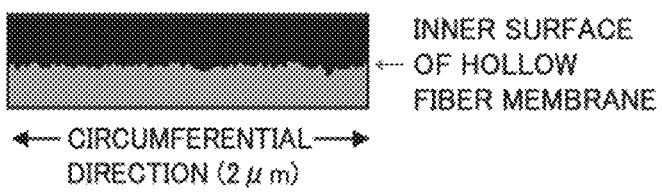
FIG. 2 illustrates unevenness on the surface in a circumferential direction when the inner surface of the hollow fiber membrane according to the present invention is observed under the atomic force microscope.

In the present invention, an average depth of the recesses is preferably less than or equal to 30 nm (FIG. 2). In a case where the depth of the recess is too long, stagnation may easily occur in flow of the fluid such as blood, permeability of β2-microglobulin and the like may be lowered, and temporal stability of permeability may be lowered, although these negative effects depend on the width of the recess. Also, the transient decrease of white blood cells may be enhanced. Also, the average depth of the recesses is preferably greater than or equal to 10 nm. In a case where the depth of the recess is too short, the rectifying effect on flow of the fluid such as blood cannot be obtained, and temporal stability of permeability may be lowered. For this reason, the average depth of the recesses is preferably greater than or equal to 15 nm.

Figure 7:
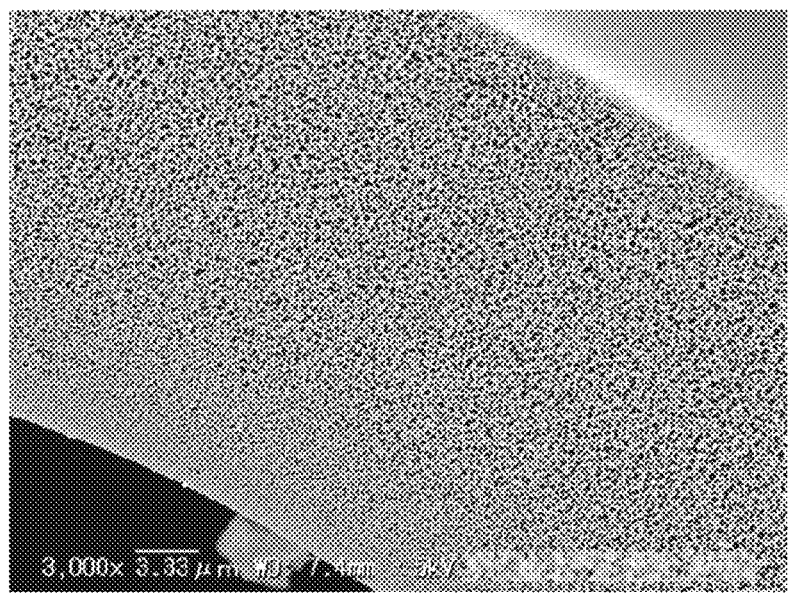
FIG. 7 illustrates an example of an image of a cross-section of the hollow fiber membrane observed at 3,000 magnification with use of a scanning electron microscope.

In the present invention, the hollow fiber membrane preferably includes a dense layer on an inner surface side thereof and preferably includes at a part other than the dense layer a pore enlarged as much as to cease to be permeation resistance to the substances. Specifically, the hollow fiber membrane includes the dense layer on the inner surface thereof and a structure causing a pore to be gradually enlarged toward an outer surface thereof or a structure causing a pore to be enlarged from the inner surface to the outer surface in the beginning, to be in an approximately equal size from a middle portion to a portion close to the outer surface, and to be enlarged or shrunk around the outer surface (FIG. 7).

In the present invention, the dense layer is a portion having no void recognized substantially in a photo (FIG. 7) obtained by capturing an image of the cross-section of the hollow fiber membrane at 3,000 magnification with use of a scanning electron microscope (SEM). Note that "substantially" means that the polymer portion and the void portion are not distinguished clearly on a photo having a normal photo size (L photo size). A thickness of the dense layer is preferably less than or equal to 2 μm, and more preferably less than or equal to 1.5 μm. In a case where a fluid to be treated (blood) is supplied to a hollow portion of the hollow fiber membrane and is subject to a treatment, the dense layer is preferably thinner from the viewpoint of lowering the permeation resistance to the substances. However, the too thin layer may cause a defect in the inner surface structure to impair the integrity of the dense layer. Thus, the thickness of the dense layer is preferably greater than or equal to 0.01 μm, and more preferably greater than or equal to 0.1 μm. Also, a support layer portion other than the dense layer may include a fine pore or a void having as large a diameter as to cease to be permeation resistance to the substances and may have as large a thickness as to enable the membrane shape to be maintained.

In the present invention, to secure flow stability of blood, an inside diameter of the hollow fiber membrane is preferably greater than or equal to 150 μm and less than 280 μm. In a case where the inside diameter of the hollow fiber membrane is too short, the linear velocity of flowing blood may be too high, and a blood cell component may be damaged when the blood flow rate is increased. Conversely, in a case where the inside diameter of the hollow fiber membrane is too long, the size of a module (blood purifier) needs to be increased to fit into the area of the membrane, and use convenience will thus be impaired.

In the present invention, a membrane thickness of the hollow fiber membrane is preferably greater than or equal to 18 μm and less than 30 μm although the membrane thickness is not particularly limited. In a case where the membrane thickness of the hollow fiber membrane is too small, permeability is enhanced, but it is difficult to maintain required strength. Also, in a case where the membrane thickness of the hollow fiber membrane is too large, permeation resistance to the substances is raised, and permeability of the substances to be removed is insufficient in some cases.

To obtain the hollow fiber membrane according to the present invention, the hollow fiber membrane is preferably formed by means of dry-wet spinning. As a spinning dope, a cellulose acetate-based polymer mixed and dissolved with a solvent and a non-solvent as needed is used. As a core solution, a coagulable solution to the cellulose acetate-based polymer is used. The spinning dope is discharged from a circular portion (slit portion) of a double-tube nozzle, at the same time, the core solution is discharged from a central hole (inner hole), and the fluid passes through an areal traveling portion and is then introduced into a coagulation bath to coagulate the shape of the hollow fiber membrane. The obtained hollow fiber membrane is washed to remove excessive solvent and the like, a membrane pore hold-back agent is impregnated into the hollow portion and the fine pore (or the void) as needed, and the hollow fiber membrane is dried and rolled up.

A technical means for obtaining the hollow fiber membrane according to the present invention will be described in detail below. To control the structure of the inner surface of the hollow fiber membrane, it is important to strictly control a process of bringing the core solution into contact with the spinning dope (dope) to form the membrane surface. That is, optimization of a discharge linear velocity ratio (linear velocity ratio) between the spinning dope and the core solution and a draft ratio is important. Specifically, in a state of using as the core solution a coagulable solution to the spinning dope containing the cellulose acetate-based polymer, it is important to set the discharge linear velocity of the spinning dope and the discharge linear velocity of the core solution to be approximately equal to each other. Here, "to be approximately equal" means to set the ratio between the discharge linear velocity of the spinning dope and the discharge linear velocity of the core solution to 0.95 to 1.05.

In the present invention, the discharge linear velocity of the spinning dope is a value obtained from the cross-sectional area of the circular portion (slit portion) and the discharge amount of the spinning dope, and the discharge linear velocity of the core solution is a value obtained from the cross-sectional area with reference to the inside diameter of the circular portion (slit portion) and the discharge amount of the core solution. For example, in a case of discharging the spinning dope at a rate of 3 cc/min. and discharging the core solution at a rate of 2 cc/min. with use of a double-tube nozzle having a slit outside diameter of 500 μm and having a slit inside diameter of 300 μm, the linear velocity ratio (discharge linear velocity of spinning dope/ discharge linear velocity of core solution) is obtained in the following manner.

Discharge linear velocity of spinning dope (m/min.) =discharge amount of spinning dope/cross-sectional area of slit portion=3 cc/$1.26 \times 10^{-3}$ cm$^2$/100=23.8

Discharge linear velocity of core solution (m/min.) =discharge amount of core solution/cross-sectional area with reference to inside diameter of slit portion=2 cc/$7.07 \times 10^{-4}$ cm$^2$/100=28.3

Linear velocity ratio=discharge linear velocity of spinning dope/discharge linear velocity of core solution=23.8/28.3=0.84

In a case where the ratio (linear velocity ratio) between the discharge linear velocity of the spinning dope and the discharge linear velocity of the core solution is too high or too low, the velocity difference between the spinning dope and the core solution is significant. Hence, turbulence of flow at the interface occurs, and the surface structure of the membrane tends to be coarse (markedly uneven). Such a phenomenon easily occurs especially in a case where the discharge linear velocity of the core solution is relatively high.

Also, in the present invention, the draft ratio represents drawing velocity from coagulation bath/discharge linear velocity of spinning dope. In order to control the structure of the inner surface of the hollow fiber membrane in the scope of the present invention, the draft ratio is preferably set to 0.80 to 0.85. For example, in a case where the drawing velocity from the coagulation bath is 50 m/min., and where the discharge linear velocity of the spinning dope is 40 m/min., the draft ratio is 1.25. When the draft ratio is high, the hollow fiber membrane whose structure is being coagulated is excessively extended. As a result, the recess formed on the inner surface is extended, and in an extreme case, a defect such as breakage of the recess occurs. Also, when the draft ratio is low, an effect of uniforming fine projections and recesses (wrinkles) generated in a lengthwise direction of the hollow fiber membrane cannot be exerted, and the rectifying effect of the fluid flowing near the inner surface of the hollow fiber membrane may not be obtained.

By employing the aforementioned conditions, the characteristic structure of the hollow fiber membrane according to the present invention can be achieved. Hereinbelow, other manufacturing preconditions for employing the aforementioned conditions will be described.

In the present invention, as the spinning dope, a cellulose acetate-based polymer mixed and dissolved with a solvent and a non-solvent is preferably used. Specifically, the spinning dope is preferably prepared with a ratio of cellulose acetate-based polymer/solvent/non-solvent=15 to 20/52 to 64/16 to 33.

In the present invention, as the solvent for the cellulose acetate-based polymer, N-methylpyrrolidone (hereinbelow abbreviated as NMP in some cases), dimethylformamide, dimethylacetamide, dimethylsulfoxide, or the like is preferably used. Also, examples of the non-solvent include ethylene glycol, triethylene glycol (hereinbelow abbreviated as TEG in some cases), polyethylene glycol glycerol, propylene glycol, and alcohols. These solvents and non-solvents have favorable compatibility with water.

In the present invention, as the core solution, an aqueous solution containing a solvent, a non-solvent, and water can be used. The core solution is preferably prepared with a ratio of solvent/non-solvent/water=0 to 14/0 to 6/80 to 100, is more preferably a mixed solution of a non-solvent and water, and is further preferably water itself. Here, examples of the water include ion-exchange water, distilled water, RO water, purified water, and ultrapure water.

The obtained spinning dope and core solution are respectively discharged from the slit portion and the central hole of the double-tube nozzle at the same time, pass through the areal traveling portion, and are then dipped into the coagulation bath to be formed in a hollow fiber shape. To obtain the hollow fiber membrane having an inside diameter of approximately 200 μm, the nozzle having a slit outside diameter of 250 to 300 μm and a slit inside diameter of 180 to 230 μm is preferably used. Also, as for the nozzle temperature, the temperature on the spinning dope side is preferably adjusted to 55 to 65° C. as a heating medium temperature, and the temperature on the core solution side is preferably adjusted to 10 to 15° C. as a cooling medium temperature.

The length of the areal traveling portion is preferably 5 mm to 100 mm depending on the spinning velocity. Also, the humidity and temperature of the areal traveling portion may be controlled as needed. After the fluid passes through the areal traveling portion, the fluid is dipped into the coagulation bath prepared with a ratio of solvent/non-solvent/water=52.5 to 56/22.5 to 24/20 to 25 to form the hollow fiber membrane. Also, the temperature of the coagulation bath is preferably adjusted to 40 to 50° C.

The hollow fiber membrane drawn from the coagulation bath is then washed with water to remove excessive solvent and non-solvent and is dipped into a glycerol bath as needed to replace water in the hollow fiber membrane with an aqueous glycerol solution. At this time, the concentration of the glycerol is preferably 85 to 93% by weight. Also, the temperature of the aqueous glycerol solution is preferably adjusted to 88 to 96° C.

After the excessive aqueous glycerol solution attached to the surface of the hollow fiber membrane is removed from the hollow fiber membrane drawn from the glycerol bath as needed, the hollow fiber membrane is dried and rolled up. The drying temperature is preferably adjusted to 35 to 60° C.

A predetermined number of the obtained hollow fiber membranes provided with crimps as needed are housed in a case to produce a module including entrance and exit of blood and entrance and exit of a dialysis fluid.

Also, since it is assumed that the hollow fiber membrane according to the present invention is used not only for hemodialysis but also under severe conditions such as hemodiafiltration and hemofiltration, the hollow fiber membrane according to the present invention has the following characteristics in addition to basic performance: water permeability (UFR) of pure water measured at 37° C. is greater than or equal to 200 ml/(m$^2$·hr·mmHg) and less than or equal to 1500 ml/(m$^2$·hr·mmHg), clearance (membrane area with reference to inside diameter: 2.1 m$^2$) of β2-MG (β2-microglobulin) measured at a filtration flow velocity of 15 ml/min. with use of bovine plasma is greater than or equal to 65 ml/min. and less than or equal to 90 mL/min., and an amount of leakage of useful protein such as albumin is less than or equal to 1.5 g/(3 L removal, membrane area with reference to inside diameter: 2.1 m$^2$).

That is, the hollow fiber membrane according to the present invention has achieved that no unnecessary blood activation occurs even after hemoconcentration resulting from filtration advances, and that high clearance of β2-MG is obtained in hemodiafiltration, in particular, postdilution hemodiafiltration. Specifically, in measurement of variation of white blood cells described below, a value after 15 minutes of start of circulation is preferably greater than or equal to 82. Also, clearance (1-hour value) of β2-MG under below-mentioned conditions is preferably greater than or equal to 70 mL/min. Also, temporal stability (4-hour value/1-hour value×100) of clearance of β2-MG under the same conditions is preferably greater than or equal to 90%.

EXAMPLES

Hereinbelow, the present invention will be described more specifically by way of examples, but the present invention is not limited to these examples.

(Measurement of Outside Diameter, Inside Diameter, and Thickness of Hollow Fiber Membrane)

The outside diameter, inside diameter, and thickness of a hollow fiber membrane are obtained by inserting an appropriate number of hollow fiber membranes into a hole of φ3 mm opened at the center of a glass slide so as not to fall, cutting the membranes along the upper and lower surfaces of the glass slide with use of a blade to obtain hollow fiber membrane cross-section samples, and measuring the short diameter and the long diameter of the hollow fiber membrane cross-section with use of a projector, Nikon-V-12A. The short diameters and long diameters of each hollow fiber membrane cross-section in two directions were measured, and respective arithmetic average values were regarded as the inside diameter and outside diameter of the hollow fiber membrane cross-section. The thickness was calculated by (outside diameter−inside diameter/2. Similar measurement was conducted for five cross-sections including a maximum cross-section and a minimum cross-section, and respective average values were regarded as the inside diameter, the outside diameter, and the thickness.

(Calculation of Membrane Area)

A membrane area A ($m^2$) of a module was obtained with reference to the inside diameter of the hollow fiber membrane.

$$A = n \times \pi \times d \times L$$

In this equation, n is the number of the hollow fiber membranes in the module, π is pi, d is an inside diameter of the hollow fiber membrane (m), and L is an effective length of the hollow fiber membrane in the module (m).

(6% Viscosity)

61.67 g of a mixed solvent [methylene chloride:methanol=91:9 (ratio by weight)] was collected in a conical flask and was charged with 3.00 g of a sample dried for two hours at 105±5° C., and the flask was tightly closed. The solution was thereafter shaken in a horizontal shaker for 1.5 hours and was further shaken in a rotary shaker for 1 hour for complete dissolution. Subsequently, the temperature of the obtained 6 wt/vol % solution was adjusted to 25±1° C. in a constant temperature oven, downflow time between mark lines for timekeeping was measured with use of an Ostwald viscometer, and the viscosity was obtained from the following equation.

6% viscosity (mPa·s)=downflow time (sec)/viscometer coefficient

Meanwhile, the viscometer coefficient was obtained from the following equation by measuring downflow time (sec) in a similar procedure to the above with use of a standard solution for viscometer calibration.

Viscometer coefficient=[standard solution absolute viscosity (mPa·s)×solution density (1.235 g/$cm^3$)]/[standard solution density (g/$cm^3$)×standard solution downflow time (sec)]

(Measurement of Hollow Fiber Membrane Inner Surface Structure)

Figure 5:
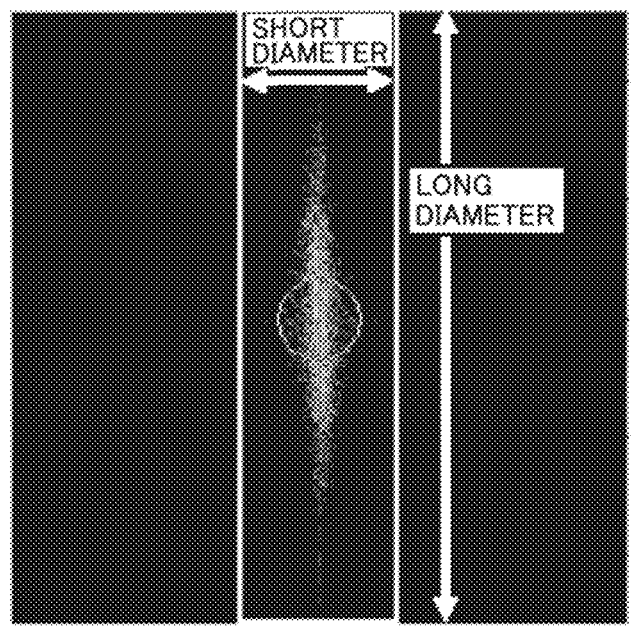
FIG. 5 illustrates an example of an image obtained by Fourier-transforming data of a recess on the inner surface of the hollow fiber membrane observed under the atomic force microscope.
Figure 6:
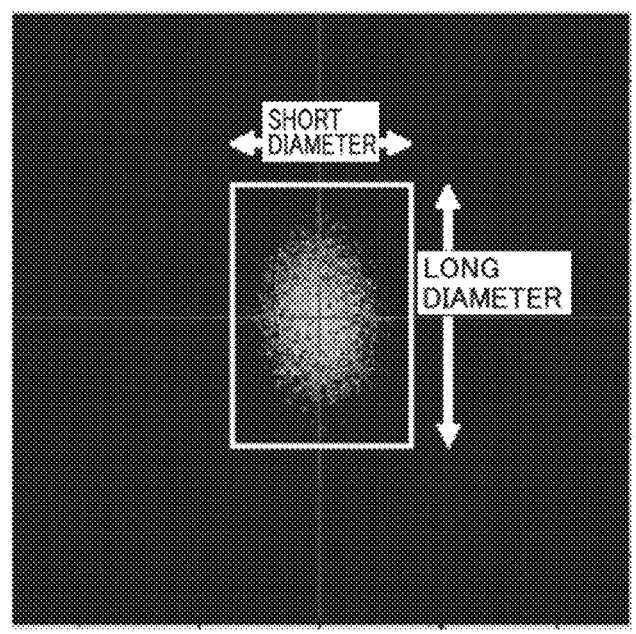
FIG. 6 illustrates another example of an image obtained by Fourier-transforming data of a recess on the inner surface of the hollow fiber membrane observed under the atomic force microscope.

The hollow fiber membrane for evaluation was used as a sample by exposing the inner surface thereof. The structure was observed with use of an atomic force microscope (AFM), E-Sweep/SPI4000 (Hitachi High-Tech Science Corporation). The observation mode was a DFM mode, the scanner was a 20 μm scanner, the cantilever was DF-3, and the observation range was 2 μm square. Planarization processing was conducted with use of attached software (SPI-Win Version 4.17F7). Also, an FFT image was produced from a planarized AFM image with use of the same software. The planarization processing optimal to the observation image is conducted by conducting two-dimensional tilt correction and Y-direction flat processing. The obtained FFT image was converted into a jpeg image, and the jpeg image was subject to an image analysis with use of image analysis measuring software WinROOF2013 (Mitani Corporation). The taken image was subject to binarization (color coordinate system: RGB, R: threshold value 0 to 170, G: threshold value 0 to 170, B: threshold value 0 to 170). Based on the obtained image, the long diameter of the recess and the short diameter of the recess were measured to calculate the aspect ratio (FIGS. 5 to 6). Five values including a highest value and a lowest value were measured to obtain the average long diameter, the average short diameter, and the average depth.

(Observation of Hollow Fiber Membrane Structure)

The hollow fiber membrane was washed lightly to remove attached glycerol. The wet hollow fiber membrane was quickly dipped into liquid nitrogen, frozen, and then taken out of the liquid nitrogen. The hollow fiber membrane was bent and cut in the frozen state to obtain a sample for cross-section observation. The obtained sample was fixed on a sample stage for carbon vapor deposition. The deposited sample was observed with use of a scanning electron microscope (S-2500 manufactured by Hitachi, Ltd.) at an acceleration voltage of 5 kV and at 3,000 magnification.

(Measurement of Variation of White Blood Cells)

Extracorporeal circulation by a dog was conducted with use of the module (membrane area: 0.5 $m^2$). As the dog, a beagle dog having a weight of approximately 15 kg was used. 50 ml/min. of blood was taken from a shunt created at the neck and flowed to the blood side (hollow portion) of the module. Meanwhile, before the extracorporeal circulation, the inside of the module was washed with saline, the module and the blood circuit were filled with saline containing 6000 IU/L of heparin, and blood flowing was started. A value for the number of white blood cells after 15 minutes of start of circulation was obtained in a case where the number of white blood cells immediately before the circulation was set to 100.

(Measurement of Clearance of β2-MG)

Measurement of clearance of β2-MG was conducted in conformity with "Postdilution" in "Performance evaluation using bovine blood" in "Performance evaluation for blood purifier 2012" provided by The Japanese Society for Dialysis Therapy. Meanwhile, the module having a membrane area, with reference to the inside diameter of the hollow fiber membrane, of 2.1 $m^2$ was used. The flow rate conditions were QBi: 500 ml/min., QDi: 700 ml/min., and QF: 80 ml/min. (Refer to NPL 1)

Example 1

17.5% by mass of cellulose triacetate (6% viscosity=162 mPa·s, Daicel Chemical Industries, Ltd.), 57.75% by mass of NMP (Mitsubishi Chemical Corporation), and 24.75% by mass of TEG (Mitsui Chemicals, Inc.) were uniformly dissolved to prepare a spinning dope. The obtained spinning dope was discharged from a slit portion of a double-tube nozzle at a rate of 1.80 cc/min., and at the same time, RO water serving as a core solution was discharged from a central hole at a rate of 2.18 cc/min. The double-tube nozzle having a slit outside diameter of 270 μm and having a slit inside diameter of 200 μm was used. The temperature of a heating medium on the spinning dope side was set to 65° C., and the temperature of a cooling medium on the core solution side was set to 10° C. The spinning dope discharged from the nozzle passed through a 25 mm areal traveling portion, was then introduced into a coagulation liquid having a temperature of 43° C. and having a ratio of NMP/TEG/water=54.6/23.4/22, and was coagulated. The coagulated hollow fiber membrane was drawn at a velocity of 57.0 m/min., washed with water, dipped into glycerol, dried, and rolled up. A bundle of the obtained hollow fiber membranes was inserted into a case, each of the ends of the bundle was attached and fixed with use of a polyurethane resin, and the resin was partially cut, to prepare a module with the ends of each of the hollow fiber membranes opened. The evaluation results were listed in Table 1.

Example 2

Hollow fiber membranes were manufactured in the same manner as in Example 1 except that the drawing velocity from the coagulation liquid was set to 55.0 m/in., and a module was prepared.

Example 3

Hollow fiber membranes were manufactured in the same manner as in Example 1 except that the drawing velocity from the coagulation liquid was set to 59.0 m/min., and a module was prepared.

Example 4

Hollow fiber membranes were manufactured in the same manner as in Example 1 except that the discharge amount of the core solution was set to 2.08 cc/min., and a module was prepared.

Example 5

Hollow fiber membranes were manufactured in the same manner as in Example 1 except that the discharge amount of the core solution was set to 2.30 cc/min., and a module was prepared.

Example 6

Hollow fiber membranes were manufactured in the same manner as in Example 1 except that the discharge amount of the spinning dope was set to 1.88 cc/min., and a module was prepared.

Example 7

Hollow fiber membranes were manufactured in the same manner as in Example 1 except that the discharge amount of the spinning dope was set to 1.70 cc/min., and a module was prepared.

Example 8

Hollow fiber membranes were manufactured in the same manner as in Example 1 except that, with use of a double-tube nozzle having a slit outside diameter of 330 μm and having a slit inside diameter of 260 rpm, the discharge amount of the spinning dope was set to 2.26 cc/min., and the discharge amount of the core solution was set to 3.70 cc/min., so that the linear velocity ratio and the draft ratio might be equal to those in Example 1, and a module was prepared.

Example 9

Hollow fiber membranes were manufactured in the same manner as in Example 1 except that, with use of a double-tube nozzle having a slit outside diameter of 250 μm and having a slit inside diameter of 180 rpm, the discharge amount of the spinning dope was set to 1.65 cc/min., and the discharge amount of the core solution was set to 1.77 cc/min., so that the linear velocity ratio and the draft ratio might be equal to those in Example 1, and a module was prepared.

Comparative Example 1

Hollow fiber membranes were manufactured in the same manner as in Example 1 except that the discharge amount of the core solution was set to 2.40 cc/min., and a module was prepared.

Comparative Example 2

Hollow fiber membranes were manufactured in the same manner as in Example 1 except that the discharge amount of the core solution was set to 2.00 cc/min., and a module was prepared.

Comparative Example 3

Hollow fiber membranes were manufactured in the same manner as in Comparative Example 1 except that the drawing velocity from the coagulation liquid was set to 62.0 m/min., and a module was prepared.

Comparative Example 4

Hollow fiber membranes were manufactured in the same manner as in Comparative Example 2 except that the drawing velocity from the coagulation liquid was set to 54.0 m/min., and a module was prepared.

Comparative Example 5

Hollow fiber membranes were manufactured in the same manner as in Example 1 except that the drawing velocity from the coagulation liquid was set to 74.0 m/min., so that the draft ratio might be 1.06, and a module was prepared.

Comparative Example 6

Hollow fiber membranes were manufactured in the same manner as in Example 1 except that the drawing velocity from the coagulation liquid was set to 54.0 m/min., and a module was prepared.

Comparative Example 7

Figure 3:
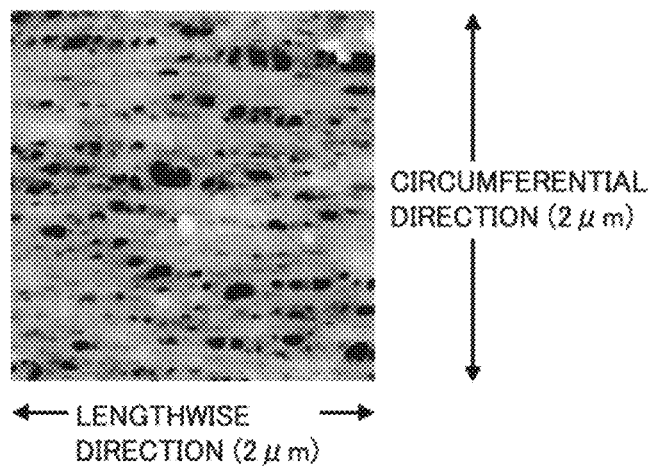
FIG. 3 illustrates a surface shape image when an inner surface of a conventional hollow fiber membrane is observed under an atomic force microscope.
Figure 4:
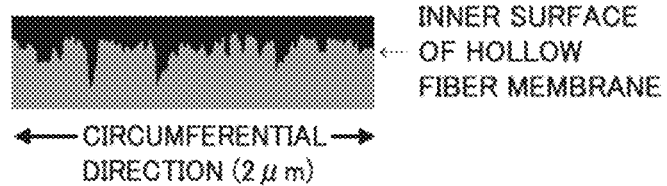
FIG. 4 illustrates unevenness on the surface in a circumferential direction when the inner surface of the conventional hollow fiber membrane is observed under the atomic force microscope.

A similar evaluation was conducted with use of a hollow fiber membrane made of polyether sulfone (manufactured by Nipro Corporation). Meanwhile, the inside diameter of the hollow fiber membrane was 200 μm, and the membrane thickness thereof was 40 μm. Also, results of observation of the inner surface of the hollow fiber membrane in Comparative Example 7 under the AFM are shown in FIGS. 3 and 4.

TABLE 1

| | Double-tube nozzle | | | Coagulation bath | | Hollow fiber membrane | | |
|---|---|---|---|---|---|---|---|---|
| | Discharge amoount of spinning dope (cc/min) | Discharge amount of core solution (cc/min) | Linear velocity ratio | Drawing velocity (m/min) | Draft ratio | Outside diameter (μm) | Inside diameter (μm) | Membrane thickness (μm) |
| Example 1 | 1.80 | 2.18 | 1.00 | 57.0 | 0.82 | 250 | 200 | 25 |
| Example 2 | 1.80 | 2.18 | 1.00 | 56.0 | 0.80 | 252 | 200 | 26 |
| Example 3 | 1.80 | 2.18 | 1.00 | 59.0 | 0.85 | 248 | 200 | 24 |
| Example 4 | 1.80 | 2.08 | 1.05 | 57.0 | 0.82 | 248 | 200 | 24 |
| Example 5 | 1.80 | 2.30 | 0.95 | 57.0 | 0.82 | 248 | 200 | 24 |
| Example 6 | 1.88 | 2.18 | 1.05 | 58.0 | 0.80 | 252 | 200 | 26 |
| Example 7 | 1.70 | 2.18 | 0.95 | 56.0 | 0.85 | 246 | 200 | 23 |
| Example 8 | 2.26 | 3.70 | 1.00 | 57.0 | 0.82 | 318 | 260 | 29 |
| Example 9 | 1.65 | 1.77 | 1.00 | 57.0 | 0.82 | 222 | 180 | 21 |
| Comparative Example 1 | 1.80 | 2.40 | 0.91 | 57.0 | 0.82 | 248 | 200 | 24 |
| Comparative Example 2 | 1.80 | 2.00 | 1.09 | 57.0 | 0.82 | 248 | 200 | 24 |
| Comparative Example 3 | 1.80 | 2.40 | 0.91 | 62.0 | 0.89 | 246 | 200 | 23 |
| Comparative Example 4 | 1.80 | 2.00 | 1.09 | 54.0 | 0.78 | 248 | 200 | 23 |
| Comparative Example 5 | 1.80 | 2.18 | 1.00 | 74.0 | 1.06 | 245 | 199 | 23 |
| Comparative Example 6 | 1.80 | 2.18 | 1.00 | 54.0 | 0.78 | 250 | 200 | 25 |
| Comparative Example 7 | | | | | | 280 | 200 | 40 |

| | Recess | | | | Decrease of white blood cells | β2-mg clearance | | After 4 hours/ after 1 hour × 100 |
|---|---|---|---|---|---|---|---|---|
| | Long diameter (nm) | Short diameter (nm) | Aspect ratio | Depth (nm) | | After 1 hour (ml/min.) | After 4 hours (ml/min.) | |
| Example 1 | 341 | 27 | 13 | 21 | 87 | 77 | 72 | 94 |
| Example 2 | 268 | 36 | 7 | 25 | 92 | 75 | 68 | 91 |
| Example 3 | 424 | 20 | 21 | 19 | 83 | 80 | 75 | 94 |
| Example 4 | 360 | 30 | 12 | 26 | 86 | 76 | 70 | 92 |
| Example 5 | 347 | 35 | 10 | 28 | 83 | 73 | 66 | 90 |
| Example 6 | 222 | 37 | 6 | 28 | 87 | 75 | 68 | 91 |
| Example 7 | 455 | 23 | 20 | 27 | 90 | 82 | 78 | 95 |
| Example 8 | 361 | 30 | 12 | 26 | 88 | 74 | 70 | 95 |
| Example 9 | 353 | 32 | 11 | 23 | 90 | 79 | 74 | 94 |
| Comparative Example 1 | 342 | 63 | 5 | 28 | 81 | 72 | 62 | 86 |
| Comparative Example 2 | 332 | 14 | 24 | 27 | 78 | 80 | 62 | 78 |
| Comparative Example 3 | 545 | 19 | 29 | 23 | 84 | 79 | 68 | 86 |
| Comparative Example 4 | 206 | 82 | 3 | 66 | 75 | 87 | 57 | 85 |
| Comparative Example 5 | 667 | 16 | 42 | 25 | 83 | 78 | 67 | 86 |
| Comparative Example 6 | 184 | 50 | 4 | 61 | 74 | 63 | 55 | 87 |
| Comparative Example 7 | 183 | 88 | 2 | 83 | 77 | 77 | 68 | 88 |

As is apparent from the results in Table 1, in Examples 1 to 9, a hollow fiber membrane excellent in biocompatibility and excellent in temporal stability of solute permeability even in postdilution hemodiafiltration therapy is obtained. Conversely, the result of Comparative Example 1 showed that a transient decrease of white blood cells occurred significantly, and temporal stability of performance was low. The reason for this may be that the average width of the recesses is long, and that the aspect ratio is low. The decrease is probably caused by clogging due to accumulation of a blood component in the recesses. Also, the result of Comparative Example 2 showed that a transient decrease of white blood cells occurred significantly, and that temporal stability of performance was low. The reason for this may be that the average width of the recesses is slightly short, and that the aspect ratio is out of the favorable range. This may be because a sufficient blood rectifying effect cannot be obtained since the average width of the recesses is short. Also, the result of Comparative Example 3 similarly showed that temporal stability of performance was low. This may be because a defect such as breakage of the recess in the lengthwise direction occurs since the draft ratio is high.

Also, the results of Comparative Examples 4 and 6 showed that a transient decrease of white blood cells occurred significantly, and that initial performance and temporal stability of performance were low. This may be because the surface of the membrane is coarse since the linear velocity ratio is high, and the draft ratio is low. Also, the result of Comparative Example 5 showed that, since the draft was too high, breakage of the recess occurred, and that, while initial performance was high, temporal performance degradation occurred. Also, in Comparative Example 7, the recess shape was out of the favorable range of the present invention. The reason for this may be a different material. The result showed that, while initial performance was high, temporal stability of performance was low.

INDUSTRIAL APPLICABILITY

A hollow fiber membrane according to the present invention has an asymmetric membrane structure containing a cellulose acetate-based polymer and including a dense layer at least on an inner surface side thereof and has high water permeability, molecular cutoff characteristics, and solute permeability. In particular, by optimizing the structure of the dense layer on the inner surface of the hollow fiber membrane, it is possible to provide a hollow fiber membrane having improved biocompatibility and having improved safety even under severe hemodiafiltration conditions to a patient with large body frame.

The invention claimed is:

1. A hollow fiber membrane comprising a cellulose acetate-based polymer,
   wherein
   when an inner surface of the hollow fiber membrane is observed under an atomic force microscope, a plurality of groove-like recesses oriented in a lengthwise direction of the hollow fiber membrane are observed,
   an average length of the recesses is greater than or equal to 200 nm and less than or equal to 500 nm,
   an average width of the recesses is greater than or equal to 15 nm and less than or equal to 50 nm,
   an aspect ratio defined as a ratio of the average length to the average width of each of the recesses is greater than or equal to 6 and less than or equal to 22, and
   the cellulose acetate-based polymer is cellulose triacetate.

2. The hollow fiber membrane according to claim 1, wherein the hollow fiber membrane includes a dense layer on the inner surface side, and a part other than the dense layer has a larger pore than that on the inner surface side.

3. The hollow fiber membrane according to claim 1, wherein an inside diameter of the hollow fiber membrane is greater than or equal to 150 μm and less than or equal to 280 μm, and a membrane thickness of the hollow fiber membrane is greater than or equal to 18 μm and less than or equal to 30 μm.

4. A hollow fiber membrane module comprising the hollow fiber membrane according to claim 1.

* * * * *